(12) United States Patent
Fried et al.

(10) Patent No.: US 11,951,318 B2
(45) Date of Patent: Apr. 9, 2024

(54) RECHARGE SYSTEM EXTENDING DEPTH AND AREA OF USEFUL RECHARGE VIA DYNAMICALLY ADJUSTED RECTIFICATION MODE

(71) Applicant: Medtronic, Inc., Minneapolis, MN (US)

(72) Inventors: Andrew Fried, Woodbury, MN (US); Todd V. Smith, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 594 days.

(21) Appl. No.: 17/079,098

(22) Filed: Oct. 23, 2020

(65) Prior Publication Data

US 2021/0121709 A1 Apr. 29, 2021

Related U.S. Application Data

(60) Provisional application No. 62/925,878, filed on Oct. 25, 2019.

(51) Int. Cl.
| | |
|---|---|
| *H02J 7/00* | (2006.01) |
| *A61N 1/05* | (2006.01) |
| *A61N 1/36* | (2006.01) |
| *A61N 1/372* | (2006.01) |
| *A61N 1/378* | (2006.01) |
| *H02J 50/10* | (2016.01) |
| *H02J 50/80* | (2016.01) |

(52) U.S. Cl.
CPC ......... *A61N 1/3787* (2013.01); *A61N 1/0551* (2013.01); *A61N 1/36125* (2013.01); *A61N 1/37223* (2013.01); *H02J 7/00032* (2020.01); *H02J 7/0042* (2013.01); *H02J 7/0048* (2020.01); *H02J 7/00714* (2020.01); *H02J 50/10* (2016.02); *H02J 50/80* (2016.02)

(58) Field of Classification Search
CPC .............................. A61N 1/3787; H02J 50/80
USPC ......................................................... 320/108
See application file for complete search history.

(56) References Cited

U.S. PATENT DOCUMENTS

| | | | |
|---|---|---|---|
| 3,522,507 | A | 8/1970 | Seiger |
| 7,248,929 | B2 | 7/2007 | Meadows et al. |
| 7,496,404 | B2 | 2/2009 | Meadows et al. |
| 8,271,089 | B2 | 9/2012 | Dinsmoor et al. |
| 9,209,634 | B2 | 12/2015 | Cottrill et al. |
| 10,080,902 | B2 | 9/2018 | Dinsmoor et al. |
| 10,411,762 | B2 | 9/2019 | Fukaya |
| 10,583,303 | B2 | 3/2020 | Maile et al. |
| 2006/0122660 | A1 | 6/2006 | Boveja et al. |

(Continued)

FOREIGN PATENT DOCUMENTS

| | | |
|---|---|---|
| EP | 2752221 B1 | 8/2016 |
| WO | WO2019209419 A1 | 10/2019 |

OTHER PUBLICATIONS

International Search Report and Written Opinion for PCT Application PCT/US2020/057225 dated Feb. 15, 2021.

(Continued)

*Primary Examiner* — Yalkew Fantu
(74) *Attorney, Agent, or Firm* — Husch Blackwell LLP

(57) ABSTRACT

Devices and methods described herein relate to wireless recharging from a distance, and increasing the efficiency of such charging by intelligently or autonomously changing the rectification mode of the implanted device.

20 Claims, 14 Drawing Sheets

(56) References Cited

U.S. PATENT DOCUMENTS

| | | |
|---|---|---|
| 2012/0197351 A1* | 8/2012 | Olson ................ A61N 1/3787 320/108 |
| 2014/0070773 A1* | 3/2014 | Cottrill .............. H02J 7/00036 320/150 |
| 2014/0163648 A1* | 6/2014 | Olson ................ A61N 1/3787 607/61 |
| 2014/0184149 A1* | 7/2014 | Jung ...................... H02J 50/80 320/108 |
| 2014/0191717 A1* | 7/2014 | Hong ..................... H02J 50/10 320/108 |
| 2016/0126771 A1* | 5/2016 | Aghassian ......... A61N 1/37229 320/108 |
| 2017/0256956 A1 | 9/2017 | Irish et al. |
| 2019/0273404 A1 | 9/2019 | Angara et al. |
| 2020/0001094 A1 | 1/2020 | Iyer et al. |
| 2020/0001095 A1 | 1/2020 | Iyer et al. |
| 2020/0061368 A1 | 2/2020 | Towe |

OTHER PUBLICATIONS

Coulombe et al, "Wireless Smart Implants Dedicated to Multichannel Monitoring and Microstimulation", IEEE Circuits and Systems Magazine. Jan. 1, 2005.

* cited by examiner

RECHARGE SYSTEM EXTENDING DEPTH AND AREA OF USEFUL RECHARGE VIA DYNAMICALLY ADJUSTED RECTIFICATION MODE

CROSS-REFERENCE TO RELATED APPLICATIONS

This application claims the benefit of U.S. Provisional Application No. 62/925,878 filed on Oct. 25, 2019, the entirety of which is incorporated herein by reference.

FIELD

The present technology is generally related to an implantable medical device and more specifically a wirelessly rechargeable implantable device that delivers a medical therapy.

BACKGROUND

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable devices can be recharged while implanted with a transcutaneous recharge signal produced by one or more field-producing coils external to the patient.

Implantable medical devices configured for recharging are typically configured with either the recharging coil internal to the medical device housing, external to the housing, or remotely located away from the housing. However the medical device recharging coil is configured, it is desirable to improve recharging efficiency for benefits such as decreased recharging time and decreased medical device temperature rise while recharging.

Many patients desire rechargeable implants that are as small as possible, and also implanted as deeply as possible. These desires, however, can conflict with system designs involving transcutaneous inductive energy transfer. Increasing implant depth of a device having conventional size past about two to three cm can result in slow and inefficient charging. For the foregoing reasons there is a need for a rechargeable implantable medical device with improved recharging efficiency, especially for small devices implanted at higher depths.

SUMMARY

The techniques of this disclosure generally relate to wireless charging improvements by dynamic adjustment of rectification mode.

In one aspect, the present disclosure provides an external charging device. The external charging device includes a first antenna and a second antenna. The first antenna is configured to output a recharge signal. The second antenna is configured to transmit and receive telemetry signals. A telemetry module is configured to receive a level of implantable medical device battery charge current from the second antenna. A processor of the external charging device is coupled to the telemetry module, the first antenna, and the second antenna, and is configured to direct the first antenna to output the recharge signal and direct the second antenna to output instructions to configure the rectification mode of a corresponding implanted device to fullwave or halfwave based upon the level of implantable medical device battery charge current.

Optionally, in some embodiments the first antenna and the second antenna are the same antenna. The processor can be configured to direct the common antenna to output the recharge signal and the instructions at different times, in embodiments. When the first antenna and the second antenna are a common antenna, the processor can be configured to combine the output instructions and the recharge signal for simultaneous transmission.

According to another embodiment, a method of wirelessly recharging an implantable medical device includes (a) emitting a recharging signal at an antenna of a wireless recharger; (b) collecting telemetry data at the wireless recharger corresponding to a level of charge current in the implantable medical device; (c) transmitting an output instruction from the wireless recharger to the implanted medical device including an instruction for a rectification mode. The output instruction is a fullwave rectification instruction when the charge current is greater than a threshold, and a halfwave rectification instruction when the charge current is less than the threshold.

The threshold can be based upon the charge current plus or minus a hysteresis value.

According to another embodiment, a system includes a wireless recharger and an implanted device. The wireless recharger includes an antenna configured to output a recharge signal and a telemetry module configured to receive a level of charge current in a battery. The implanted device includes a battery and a device telemetry module configured to transmit a level of charge current in the battery. A processor of the implanted devices is configured to direct the implanted device to operate in a fullwave rectified wireless signal or a halfwave rectified wireless signal based upon the level of charge current The processor can be arranged in the wireless recharger, in an embodiment, or in another embodiment it can be arranged in the implanted device.

According to another embodiment, a system comprising an external charging device includes at least one antenna configured to output a recharge signal. The system further includes an implanted device configured to receive the recharge signal and operate in any of at least two modes of rectification of the recharge signal to charge the implanted device, and a processor configured to determine the optimal rectification mode for the implant to be operating according to an algorithm.

In embodiments, the processor applies the algorithm to compare a charge current in the implanted device against a threshold plus or minus a hysteresis value to determine which rectification mode is more optimal. The processor can be configured to compare a peak voltage of the rectified recharge signal plus or minus a hysteresis value to operate the implanted device in the rectification mode that results in greater charge current. The processor can be configured to compare a sensed magnetic field at the implanted device to a threshold to operate the implanted device in the rectification mode that results in greater charge current. The processor can be a microcontroller arranged within the implanted device. The antenna can be configured to receive information pertinent to the optimal rectification mode transmitted by the implanted device at an out-of-band frequency such that the recharge signal can be maintained continuously by the external charging device. The antenna can be configured to receive information pertinent to the optimal rectification mode that is superimposed with the recharge signal.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, rechargeable implantable devices that require electricity are charged by the application of an electromagnetic field to the device. The appropriate amount and direction of field used to charge the device varies based upon the orientation and type of the device itself, and in particular the orientation and type of receiver coil contained in the implantable device. Commonly used receiver coils are ferrite surrounded by a coil of conductive material, which is in turn electronically coupled to power storage.

Typical implantable devices receive power for some period of time, and then operate solely on battery power until the next recharging. It is generally desirable for the period of time for charging to be as short as possible, and the amount of operation time before recharging is required to be as long as possible. There are multiple factors that can be modified to achieve these results, such as battery size, materials used, and efficiency of the devices themselves. Some factors that are controllable but may adversely affect charging efficiency is the size of the implanted device and the depth of implantation. In general, the deeper the device is implanted and the smaller the device, the more challenging it is to efficiently recharge the implanted device wirelessly.

Figure 1:
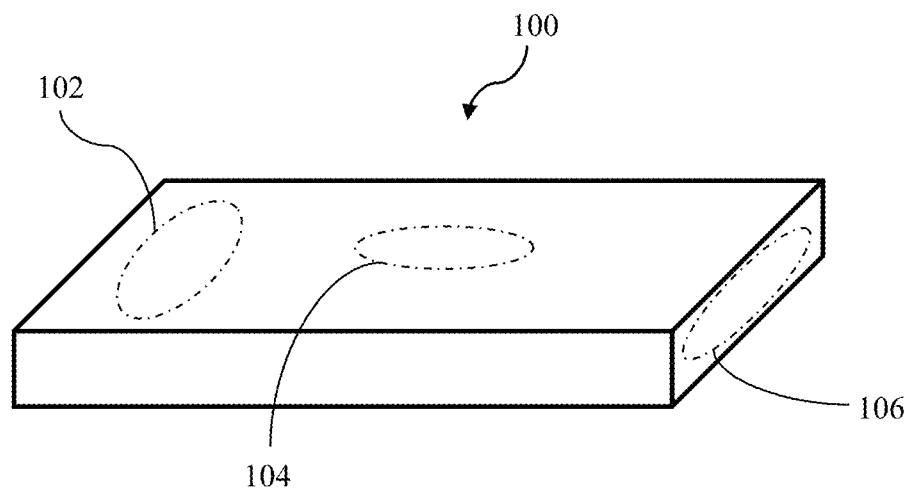
FIG. 1 is a simplified schematic view of an implantable device depicting possible receiving coil locations.

FIG. 1 depicts a simplified, rectilinear implantable device 100. Device 100 can have a receiver coil arranged at various locations, indicated as regions 102, 104, and 106. At any of these regions 102, 104, 106, a receiver can be arranged either inside of or on the outer surface of device 100. The choice of where to position the receiver coil has a direct impact on the type of charging field that will be the most effective. Specifically, the magnetic field should be strongest at, and oriented along the primary axis of, the receiving coil. Charging via a receiver coil arranged in an "up-down" orientation (referring to the orientation of the page) at region 104 is best accomplished by a similarly-oriented field targeted to the center of the device. Charging via a receiver coil arranged in either of the other two regions 102, 106 shown in FIG. 1 is best accomplished with a field that goes front-to-back (referring again to the orientation of the page).

It should be understood that receiving coils can be arranged at almost any location in an implantable device, and that the devices themselves often incorporate more complex geometries than a rectilinear box. The two primary directions for best charging, however, are those described above (i.e., either parallel to or orthogonal to the plane along which the device primarily extends).

Figure 2:
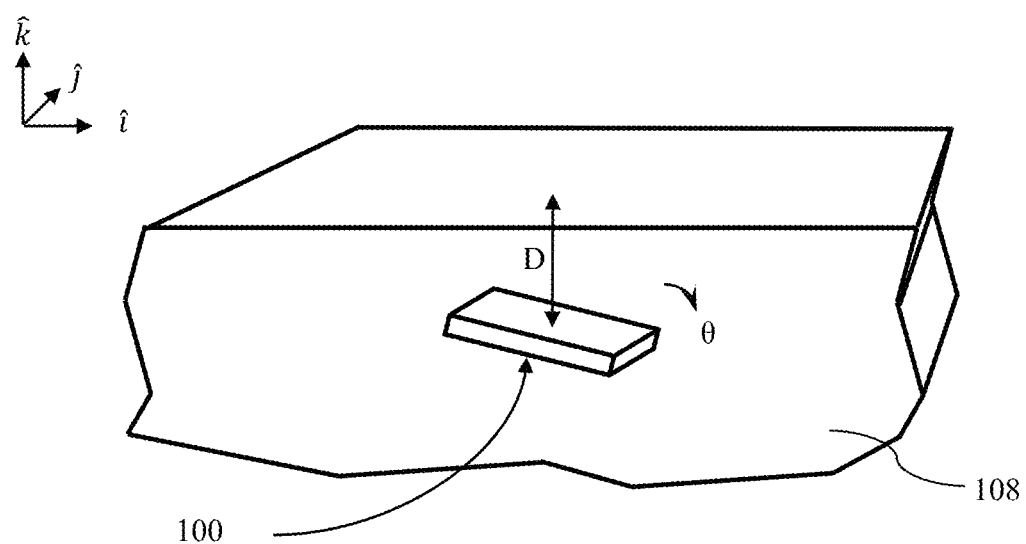
FIG. 2 is a schematic cutaway view of an implanted device depicting depth and tilt of the implanted device.

As shown in FIG. 2, the device 100 is implanted in a patient's body 108 at a depth D, and at an angle θ away from perfectly parallel to the skin. Commonly, devices may be implanted at a depth of about two cm to about three cm, and the angle θ should be as close to 0° as possible. In some cases, a surgeon may implant the device 100 at a depth D greater than the optimal maximum for that device, which reduces charging efficiency because a field generated by an external recharger will not be as strong at greater depths. Likewise, the surgeon may implant the device 100 at an angle θ that is non-zero.

Even if the device is initially implanted in acceptable (or even ideal) depth D and angle θ, these metrics can vary over time after implantation. The angle θ, depth D, and the overall position of the device 100 over time can vary in any of the i, j, or k directions indicated by the coordinates in the drawing. This variation can occur because of migration within the body, for example, or if the patient experiences physiologic changes, such as a change in body weight.

The electromagnetic field generated by an external recharger (such as, for example depicted in FIGS. 11A-12) becomes less effective as D increases, as well as when θ increases. Likewise, device 100 becomes less sensitive to incoming charging fields with decreasing size, and therefore a small device 100 at a high depth D or sufficiently large angle θ may be difficult to effectively recharge.

The instant application solves the problem of reduction of recharge efficiency due to implantable device depth and size in a way not previously contemplated. Specifically, the embodiments described herein operate using varying rectification modes. In embodiments, a desired minimum duration to remain in a particular rectification mode can be transmitted. The charge current from an implanted device can be transmitted and a rectification mode can be either maintained or modified during a charging session, either manually or automatically. Automatic changes in rectification modes can depend upon a sensed incident magnetic field. Because the devices and methods herein accommodate variations from the ideal depth D and angle θ, devices can continue to be used even as they migrate over time or if a patient gains weight. Furthermore, the devices and methods described herein permit for deeper implants of devices 100, and for the use of smaller devices 100, which are both generally desirable to patients.

The embodiments described herein are described for purposes of implanted medical devices. However, it should be understood that the charging devices and methods described throughout this disclosure are applicable to other wirelessly-recharged devices. The general goals of preventing overheating, charging at a distance, and increasing charging speed or efficiency are applicable in a number of existing fields, such as the charging of cellular phones, automobiles, telemetry devices such as sensors, monitors, and mesh network nodes, laptop computers, or near-field devices (devices operating on WiFi, NFC, Bluetooth, Zigby, etc.) that would otherwise need to be plugged in for recharging.

One example of medical devices that could implement embodiments described herein is Medtronic's INTERSTIM® or Axonics's R-SNM® sacral nerve stimulation systems. Other wirelessly recharged implantable devices, such as neurostimulators, spinal stimulators including the PRODIGY MRI™ spinal cord stimulation system from Abbott, or even deeper implanted devices such as pacemakers could be wirelessly recharged as described herein.

Figure 3:
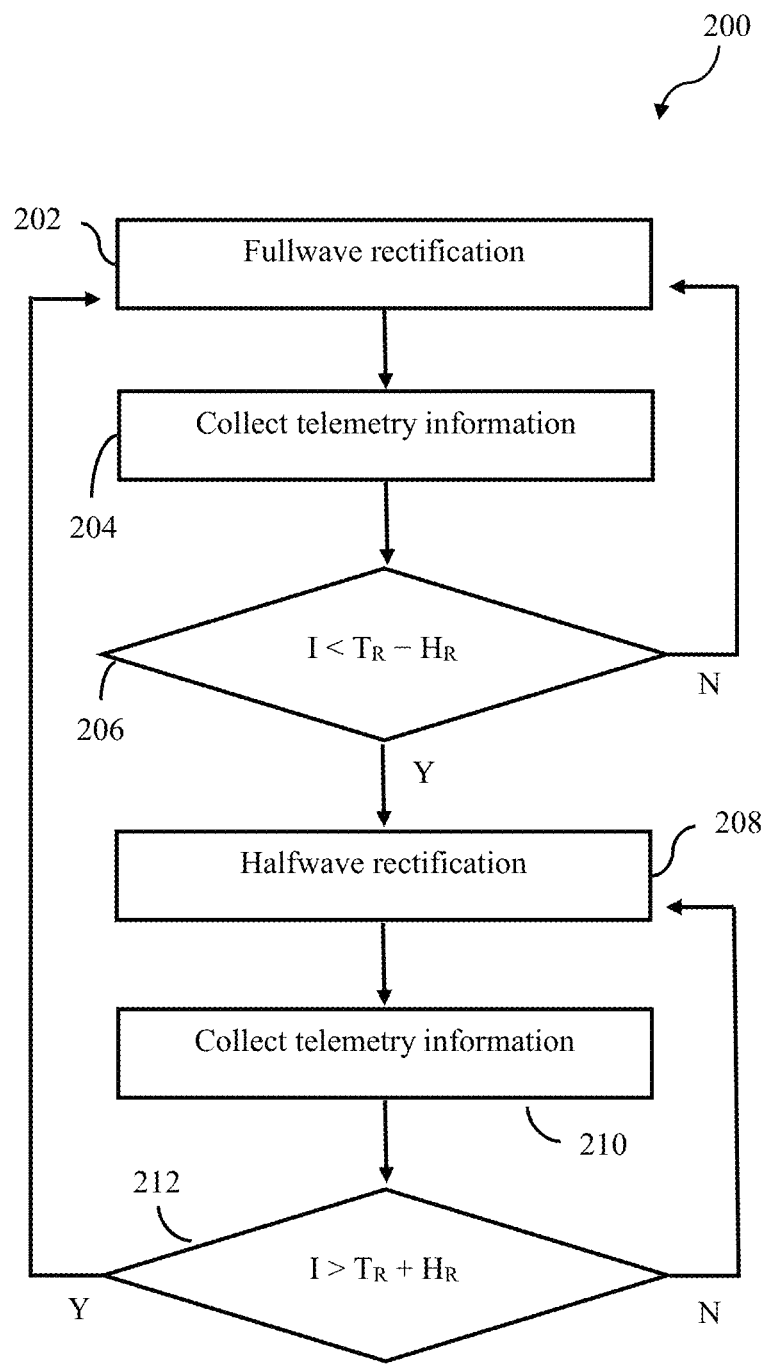
FIG. 3 is a flowchart depicting a method of setting the rectification mode of an implanted medical device, according to an embodiment.

FIG. 3 depicts a flowchart of a method 200 of operation of a device such as the device 100 previously described with respect to FIGS. 1 and 2. According to an embodiment, devices operating according to the method 200 are capable of rectifying coil voltage in either of at least two modes: fullwave and halfwave. Each of these modes provides certain benefits with respect to charging or heat generation rate, and therefore method 200 can be used to provide an improved user experience.

In one embodiment, fullwave rectification is preferred, and is therefore the default mode of operation. As such, fullwave rectification 202 is shown as the initial and default state for method 200. Halfwave rectification can be preferable when a recharger is at or near full power and the device charge current is low. These conditions can occur when the coupling between an implanted device (or other wirelessly recharged device) and the wireless recharger is poor, for example. Specific algorithms are disclosed with respect to FIG. 3, but it should be understood that other implementations could be used that use fullwave in the default or "normal" condition, and change to halfwave rectification when coupling between the charger and the device to be charged is poor.

At 204, telemetry data is collected. The telemetry data is at least indicative of recharge quality. In embodiments, the recharge quality can be determined by the charge current in the device, the voltage at the charged device, change in battery charge level over time, temperature, time spent in a particular charging rectification mode, or other similar indicators. Telemetry data can be collected at 204 on a set frequency, continuously, or on demand.

At 206, a determination is made regarding whether to switch the rectification mode. As shown in the diamond 206, charge current I (the current at the implanted device or other wirelessly recharged device) is compared to a difference of a rectification threshold $T_R$ and a rectification hysteresis $H_R$. If the charge current is still at or greater than this difference, then fullwave rectification continues at 202. On the other hand, if the charge current exceeds this difference, then the method 200 calls for switching the rectification to halfwave rectification at 208. In embodiments, the decision at diamond 206 requires that the condition $I<Tr-H_R$ remain true for some predetermined quantity of time, referred to herein as a Rectification Count Limit.

The symbols used in FIG. 3 at 206 and 212 are "less than" and "greater than," respectively, but it should be understood that in some embodiments the boundary condition ($I=T_R-H_R$ or $I=T_R+H_R$, respectively) could be dealt with differently. For example, at 206 the condition $I=T_R-H_R$ could result in switching to halfwave rectification, or it could result in continuing a loop of telemetry and fullwave rectification. Likewise, at 212 the condition $I=T_R-H_R$ could result in switching to fullwave rectification, or it could result in continuing a loop of telemetry and halfwave rectification.

In the event that the charge current is low enough that the switch is made to halfwave rectification current at 208, the rectification count is cleared and the process restarts, but with the opposite conditions. That is, halfwave rectification is used at 208, and telemetry information is collected at 210, comprising the same or similar data that was collected at 204. On the basis of the telemetry information collected at 210, a decision is made at 212 whether to remain in halfwave rectification mode 208, or whether to switch back to fullwave rectification at 202. The decision when the device has already entered halfwave rectification mode at 208 is whether charge current I exceeds the sum of the rectification threshold $T_R$ and the rectification hysteresis $H_R$.

In addition to a determination that halfwave rectification would provide more charge current, there can also be situations in which method 200 switches between fullwave and halfwave in other exceptional circumstances. Exceptional circumstances can be related to heating, for example, or due to large or unexpected changes in charge current delivered to the implanted device.

Heating can be measured, either with a temperature sensor or by a model that is based upon the amount of charge current. In general a well-paired implanted device that is not angled far from the ideal charging angle will heat more rapidly. Fullwave rectification also tends to result in more rapid heating of the charging coil, which is the product of the square of the primary coil current root mean squared, and the primary coil resistance. Unexpected changes in current in the primary coil current can also indicate a significant decrease in coupling with the implanted device, and upon receiving data at 204 or 210 indicative of such a change there could be an immediate cessation of the wireless recharge or a modification to the charging mode.

Method 200 improves charging capacity for existing devices and enables the use of new, smaller, or deeper-implanted devices. Fullwave rectification is more efficient than halfwave rectification at shallow depths and good coupling positions. Conversely, halfwave rectification is more efficient for deeply-implanted devices or at tilted angles where charge current is low. Initial results indicate that systems which were previously rechargeable up to three cm can be wirelessly recharged efficiently at depths of over four cm or even over five cm using method 200, or when tilted up to 45° from the ideal (i.e., θ=0 in FIG. 1 or 2) angle.

Whether for exceptional circumstances or based upon charge current level detection, it is also possible for the rectification mode at the implanted medical device to be toggled between fullwave and halfwave by the implanted medical device itself, without receiving any instruction from the wireless recharger.

Figure 4:
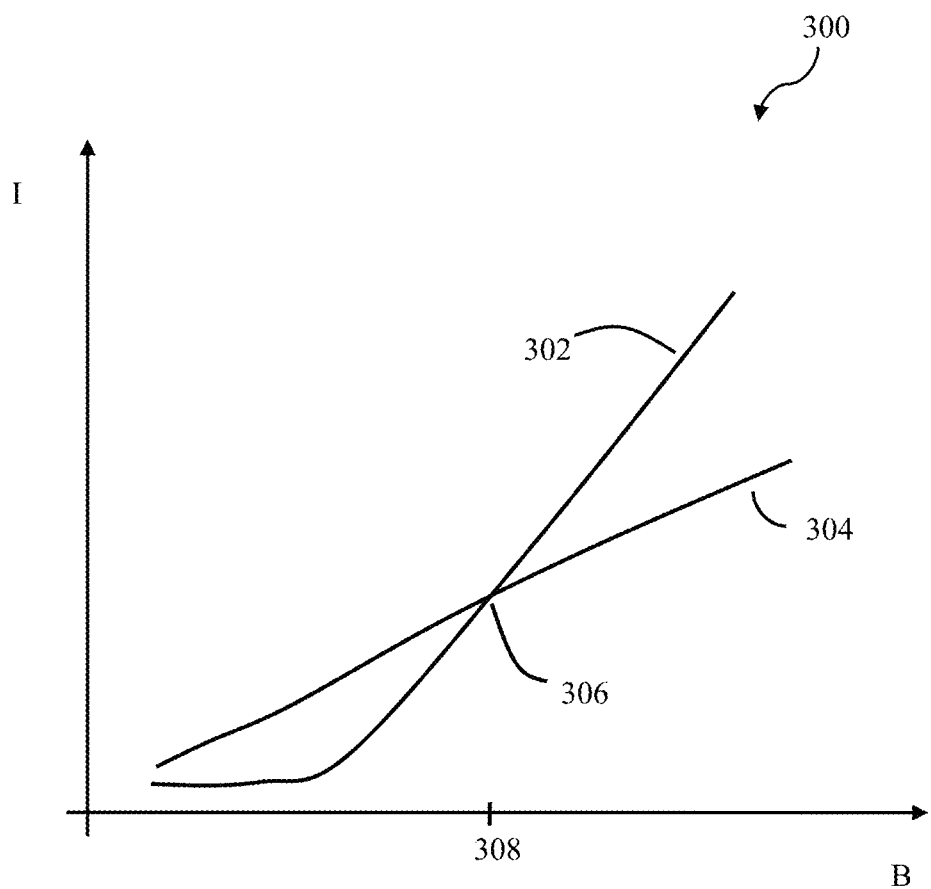
FIG. 4 is a graph of charge current in a rechargeable device against magnetic field, according to an embodiment capable of operation in two rectification modes.
Figure 5:
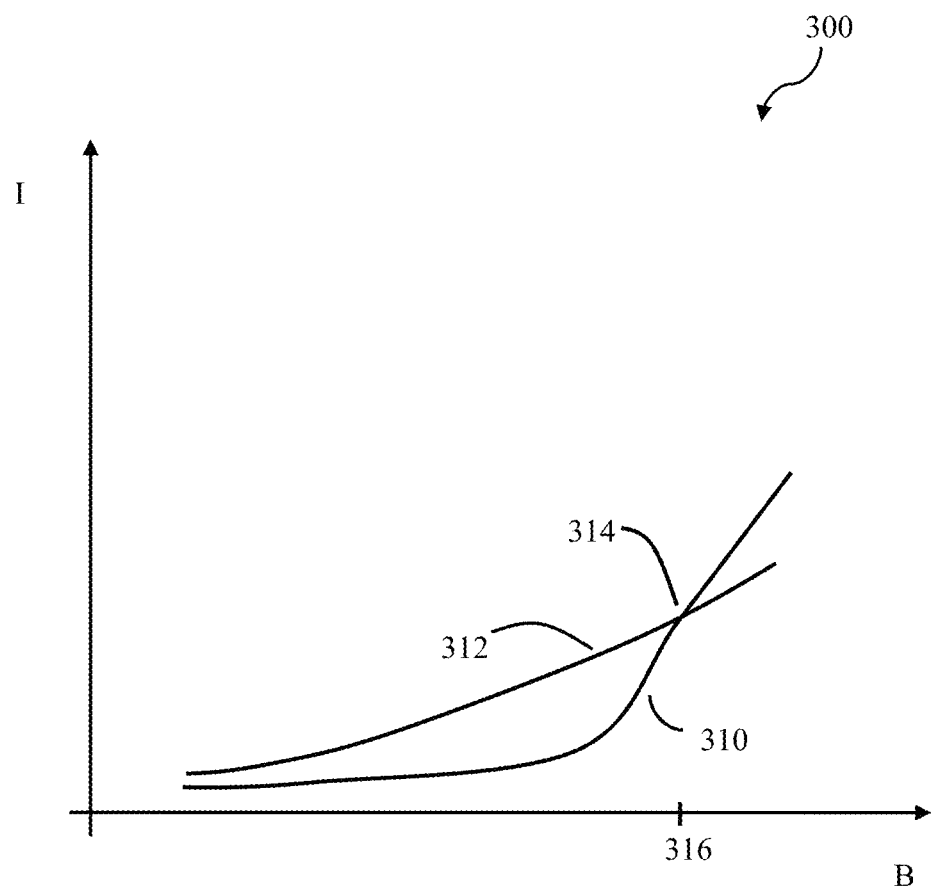
FIG. 5 is a graph of charge current in another rechargeable device against magnetic field, according to an embodiment capable of operation in two rectification modes.

FIGS. 4 and 5 each depict a graph 300 of charge current I as a function of applied magnetic field B, according to embodiments of the present disclosure. FIG. 4 is a graph of current I as a function of applied magnetic field B for a device (e.g., 100) that is implanted at an ideal angle for recharging (i.e., θ=0° in FIG. 2). In contrast, FIG. 5 is a graph of current I as a function of applied magnetic field B for the same device (e.g., 100) that is either implanted 45° away from the ideal angle, or which has migrated to 45° away from the ideal angle for recharging.

In FIG. 4, the graph 300 includes two curves. Curve 302 corresponds to the charge current in the implanted device caused by a wireless recharger operating using fullwave rectification, as a function of applied magnetic field B. Curve 304, in contrast, corresponds to the charge current in the same implanted device caused by a wireless recharger operating using halfwave rectification.

As shown in FIG. 4, the charge current curves for fullwave rectification (302) and halfwave rectification (304) cross one another at intersection 306. Thus, depending upon the field strength applied, either fullwave rectification current curve 302 or halfwave rectification current curve 304 may be higher. In particular, below threshold 308 recharging of the device will be accomplished more efficiently using halfwave rectification (i.e., halfwave rectification current curve 304 is higher than fullwave rectification current curve 302) while above threshold 308 recharging of the device will be accomplished more efficiently using fullwave rectification (i.e., fullwave rectification curve 302 is higher than halfwave rectification curve 304).

Depending upon the device, the location of implant, or even temperature of resonance frequency of the recharger or the implanted device, the exact threshold 308 can vary. In fact, threshold 308 often be inconstant as a function of time even for the same device in the same location, due to changes in temperature or other environmental conditions during the charging session.

FIG. 5 depicts the same graph 300 comparing charge current I to applied magnetic field B. In contrast to the graph 300 when shown in FIG. 4, the graph 300 in FIG. 5 shows I vs. B for a device that is angled at 45° from the ideal charging position, either due to being implanted off-axis or due to migration. It should be understood that in other embodiments the angle at which the device is rotated from the ideal charging angle could be any other amount, and that 0° and 45° are used in FIGS. 4 and 5, respectively, by way of example only.

In FIG. 5, fullwave rectification curve 310 produces substantially lower current I at the same magnetic field B, compared to the un-angled device as shown and described with respect to fullwave rectification curve 302 in FIG. 4. Likewise, halfwave rectification curve 312 is lower than its counterpart 304 as shown in FIG. 4.

As previously described with respect to the un-angled device curves of FIG. 4, in FIG. 5 the fullwave rectification curve 310 crosses the halfwave rectification curve 312 at an intersection 314. At magnetic fields exceeding the threshold 316 corresponding to the intersection 316, the fullwave rectification curve 310 produces greater charge current for the same applied magnetic field B, while at magnetic fields less than the threshold 316 the halfwave rectification curve 312 provides higher charge current for the same applied magnetic field.

In general, it is desirable to recharge an implanted device (or any other wirelessly rechargeable device) as quickly as possible, which means maximizing charge current I. In both FIGS. 4 and 5, fullwave rectification curves (302, 310) exhibit higher charge current than the halfwave rectification curves (304, 312) at the same applied magnetic field above the thresholds (308, 316). However, the exact threshold (308, 316) at which this change occurs varies. In general, the threshold (e.g., 308, 316) will be a function of the orientation of the device that is being recharged.

Applied magnetic field B is dependent upon the depth of the device (e.g., D in FIG. 2). The deeper the device is implanted, the lower the applied magnetic field will be due to spread of magnetic flux over a greater volume. Accordingly, the threshold and the applied field will vary based on the depth and orientation of the device within the patient.

Other factors such as frequency, temperature, or charge level of the battery, can affect the rate of recharge and the desired charge mode (fullwave or halfwave). In one embodiment, in addition to the method 200 shown in FIG. 3, the battery charge level can be considered to determine whether to switch between fullwave or halfwave recharging. A device that is recharging from a state where the battery has been depleted may be charged as rapidly as possible (that is, maximizing I) using fullwave rectification, for example. However, once the device is fully recharged, it may still be wirelessly connected to the recharger. In that case, halfwave recharging may be preferable for other reasons, such as reduced heating or reduced power usage.

In embodiments, a device can implement a heat control algorithm to switch back and forth between fullwave and halfwave at a defined frequency to prevent discomfort or injury to the patient. The heat control algorithm can be operated "on top of" the method 200, for example, to maximize charge current while also reducing the chances of overheating. The heat control algorithm can operate based on a timer or, in some embodiments, a charge counter (as described below in more detail with respect to FIG. 9).

Figure 6:
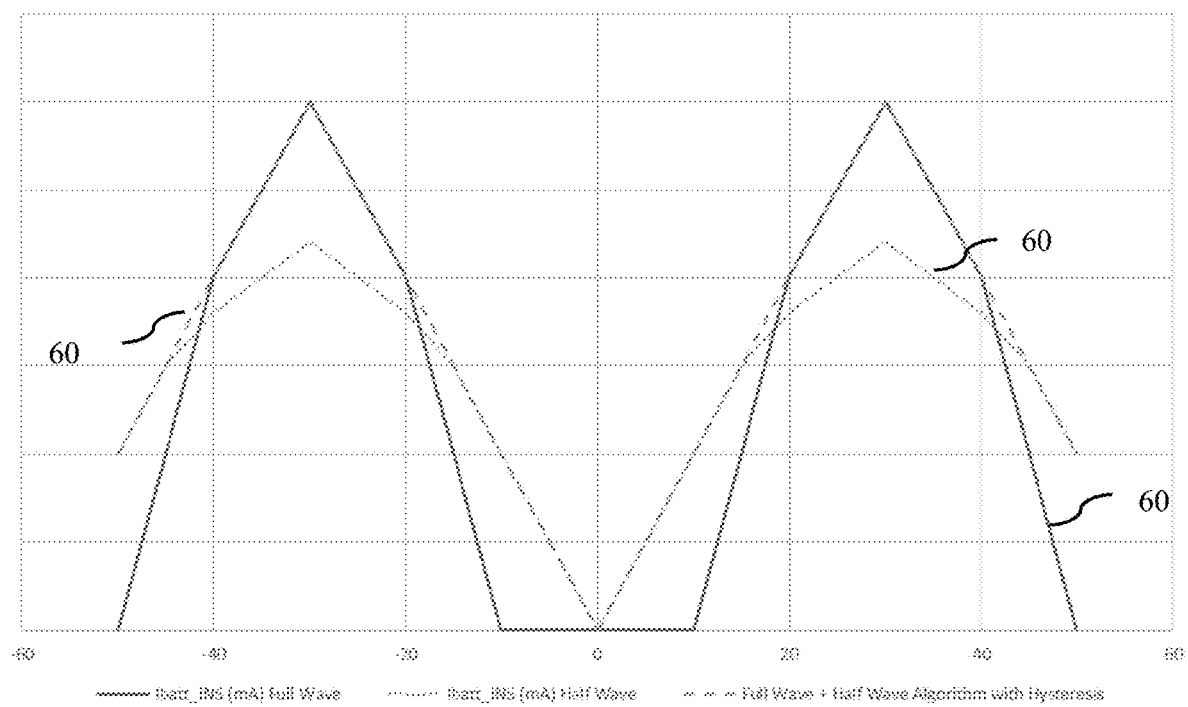
FIG. 6 is a chart showing regimes in which half- and full-wave rectification can be used to induce higher charge current for a recharger and accompanying rechargeable device.

FIG. 6 is a chart showing regimes in which half- and full-wave rectification can be used to induce higher charge current for a recharger and accompanying rechargeable device. Specifically, FIG. 6 shows recharge current induced in a rechargeable device that is tilted (e.g., near 90 degrees) relative to the recharger. This results in two lobes of effective charging position and the x-axis of FIG. 6 is the distance from center of the INS device orthogonal to the axis the device was rotated around.

As shown in FIG. 6, tilt of the rechargeable device (and specifically the receiver coil) as described above with respect to FIG. 2 creates a situation in which ideal charging or recharging conditions are both a function of relative position between the charger/recharger and the charged/recharged device, as well as the rectification mode of the charging/recharging field.

Specifically, FIG. 6 depicts the charge current that would be induced in an embodiment of an implanted medical device based upon an assumed 90° tilt of the device relative to the recharger. Line 600 shows the charge current induced by a full-wave recharging field, line 602 shows the charge current induced by a half-wave recharging field, and line 604 shows the charge current induced by the full and half wave algorithm with hysteresis described herein.

Because the device is tilted 90°, a recharger positioned directly above the device (i.e., at 0 on the x-axis) results in no charge current in the device. At an offset to either side, however, recharge current shows a peak no matter which rectification mode is used. Depending on the amount of distance away from x=0, the half-wave or full-wave rectification modes provide more charge current.

As shown in FIG. 6, the algorithm that selects between full- and half-wavelength rectification modes and considers hysteresis as described herein provides the highest level of charge current of the lines 600, 602, and 604.

Figure 7:
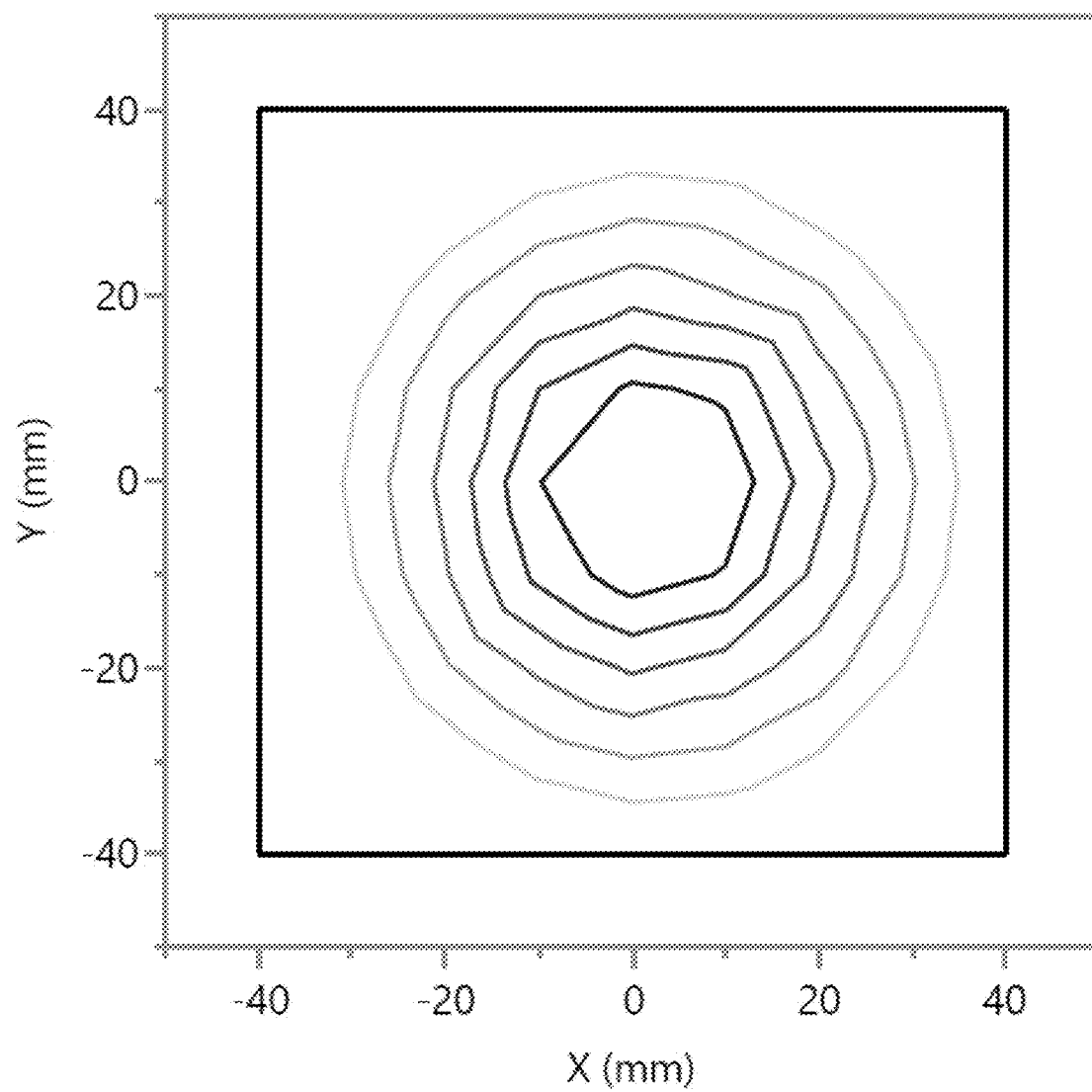
FIG. 7 is a chart of induced recharge current as a function of relative position between a recharger device and a rechargeable device at a 0° tilt relative to one another, according to an embodiment.

FIG. 7 is a graphical representation of induced charge current when the charging/recharging device is not tilted relative to the device that is being charged or recharged. In this situation, the peak recharge current occurs as the recharger is placed directly above the implanted device and the field is running parallel the skin when it interacts with the receiver coil.

The comparison between FIGS. 6 and 7 shows that especially for tilted devices (such as implanted medical devices that have shifted or were placed at an angle from their ideal position) the full- and half-wave rectification selection described herein provides advantages in that it can be used to increase charge current without relying on an assumption of peak current directly above the device. As shown in FIG. 6, placing the recharger directly over the device and using either full- or half-wave rectification would lead to very little, if any, charge current, whereas using the embodiments described herein that charge and a physical offset and by selectively determining which rectification mode to use, charge current can be increased.

Figure 8A:
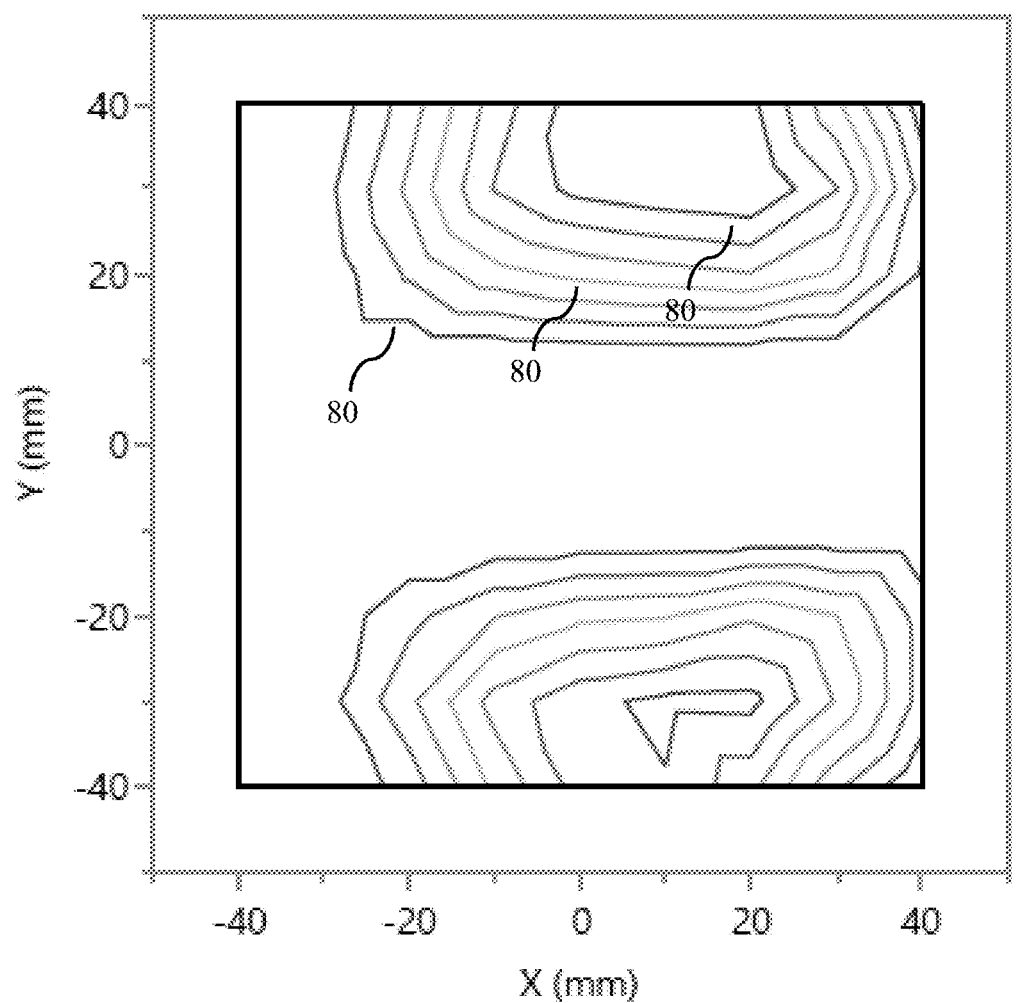
FIGS. 8A-8C are charts of induced recharge current as a function of relative position between a recharger device and a rechargeable device at a 90° tilt relative to one another, according to an embodiment.
Figure 8B:
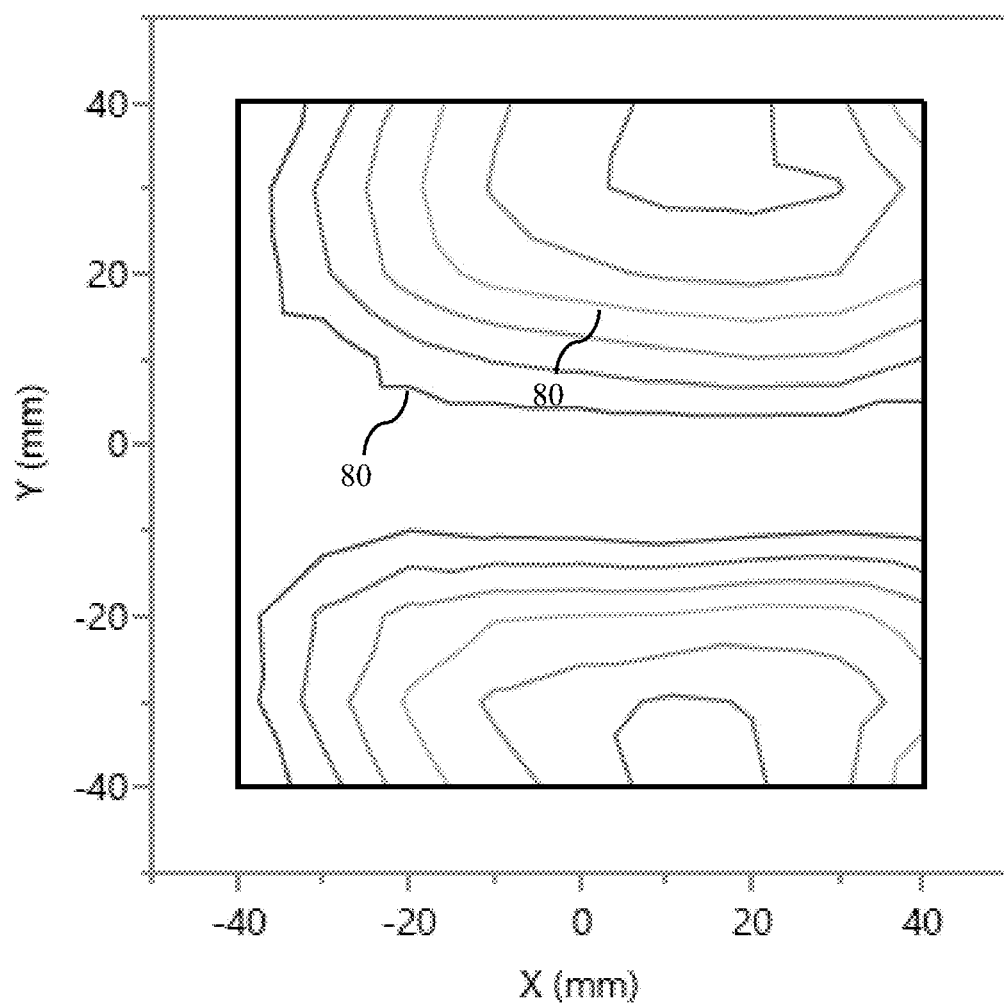
Figure 8C:
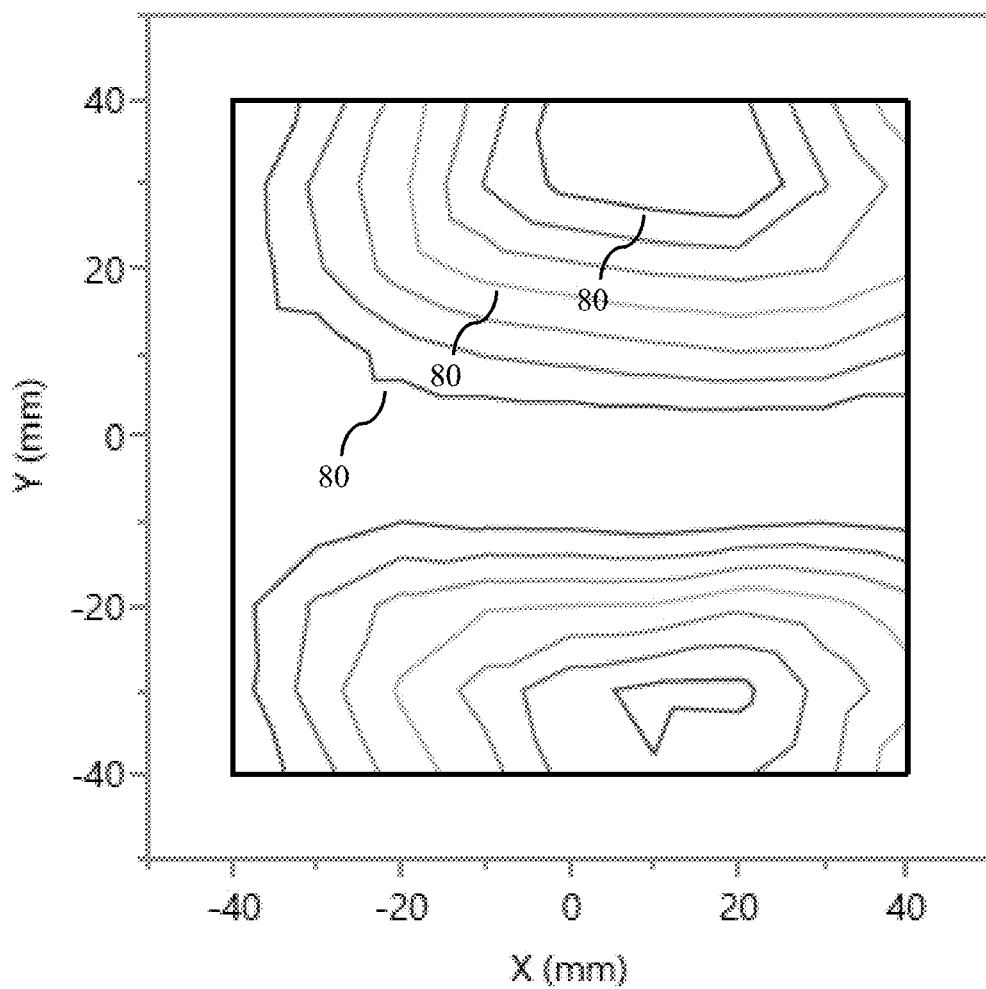

FIGS. 8A-8C show induced recharge current as a function of relative position between a recharger device and a rechargeable device at a 90° tilt relative to one another, according to an embodiment. FIG. 8A shows the charge current induced by a recharging device using full-wave rectification exclusively, while FIG. 8B shows the charge current induced by a recharging device using half-wave rectification exclusively.

Isometric lines 800, 802, 804 show equivalent levels of charge current between the three views in FIGS. 8A-8C. As shown by the comparative sizes of the regions encircled by the isometric line 800, the combination rectification mode of FIG. 8C provides the largest physical area in which recharge is possible. As shown by the comparative sizes of the isometric lines 802, higher charge current levels are accomplished over a larger area as well. And as shown by the isometric lines 804, the largest area for very high recharge levels are provided by the mode of FIG. 8C as well (in fact, FIG. 8B does not have any area that accomplishes this level of recharge whatsoever).

What this means overall for the patient or medical practitioner is that it is much easier to position a recharging device over an implanted medical device and have a good charge rate. The positioning of the recharger need not be as exact to get good (or even great) recharge speed, compared to devices relying on only one or the other rectification mode. The practitioner or patient does not need to manually adjust anything to select a recharge mode; instead, the devices themselves determine based on charge current and hysteresis which mode is better for a particular relative orientation and position of the recharger and the device.

Figure 9:
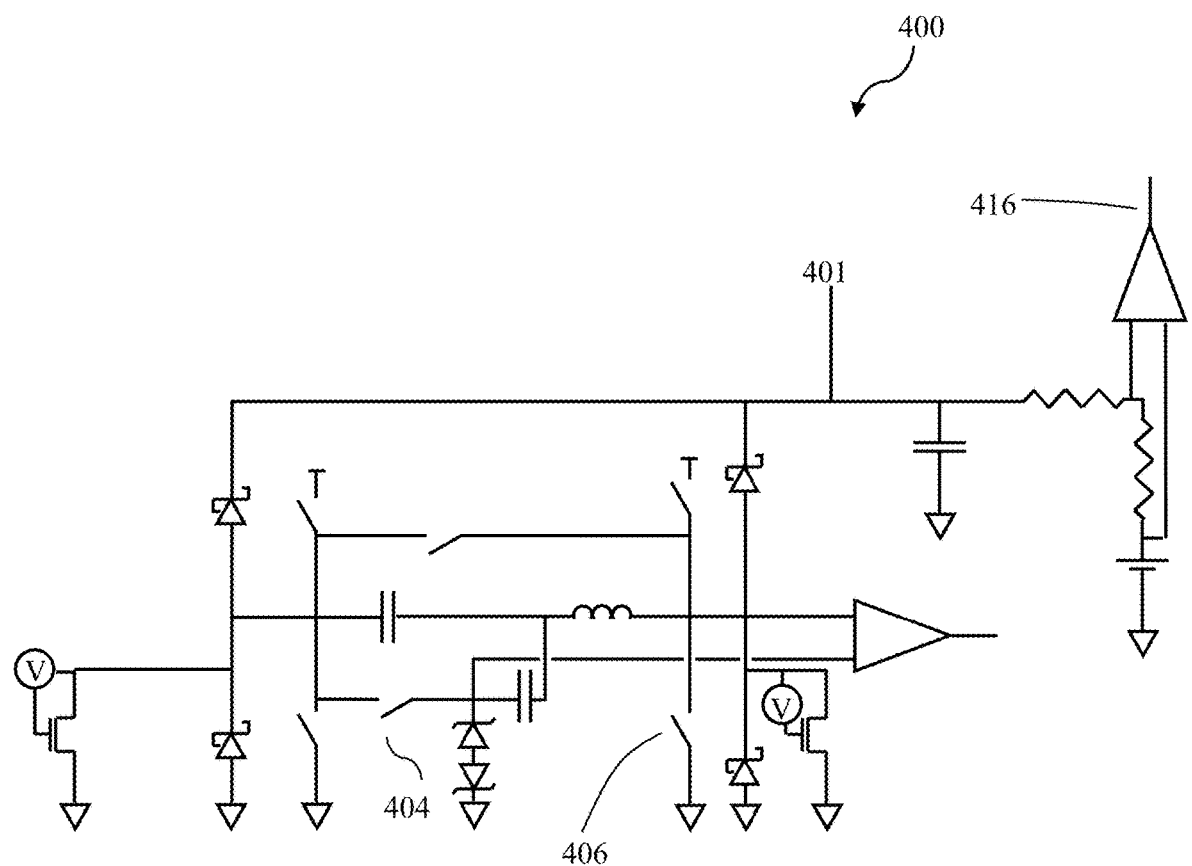
FIG. 9 is a circuit diagram of a wireless recharging circuit for an implantable medical device configured to recharge using either of two rectification modes, according to an embodiment.

An example circuit diagram of a recharging receiver is shown in FIG. 9. FIG. 9 shows a circuit 400 that includes a rectified output 401. Although there are a large number of combinations of switch positions possible, there are only a few main modes of operation, described in more detail below.

Recharge—fullwave. In fullwave rectification mode, switch 404 is closed. In this mode, the output at 401 is fullwave rectified.

Recharge—halfwave. In halfwave rectification mode, switch 404 is closed as well as switch 406. In this mode, the output at 401 is halfwave rectified.

In each of these modes, the total current delivered is measured at 416. Switching between fullwave or halfwave recharge can be accomplished either for increased current flow (as described with respect to FIG. 3) or to reduce heating, or can be based upon an elapsed time in any given recharge mode. In embodiments, the implanted device can send signals to indicate the level of charge current, as well as data that indicates an amount of time spent charging in any given mode or a level of heat dissipation. In some embodiments, the device can transmit a desired minimum duration to remain in a given rectification mode, and (based upon any combination of these data) the charger can automatically change rectification modes depending upon the sensed incident magnetic field, charge delivered, heat generated, or time elapsed.

Figure 10:
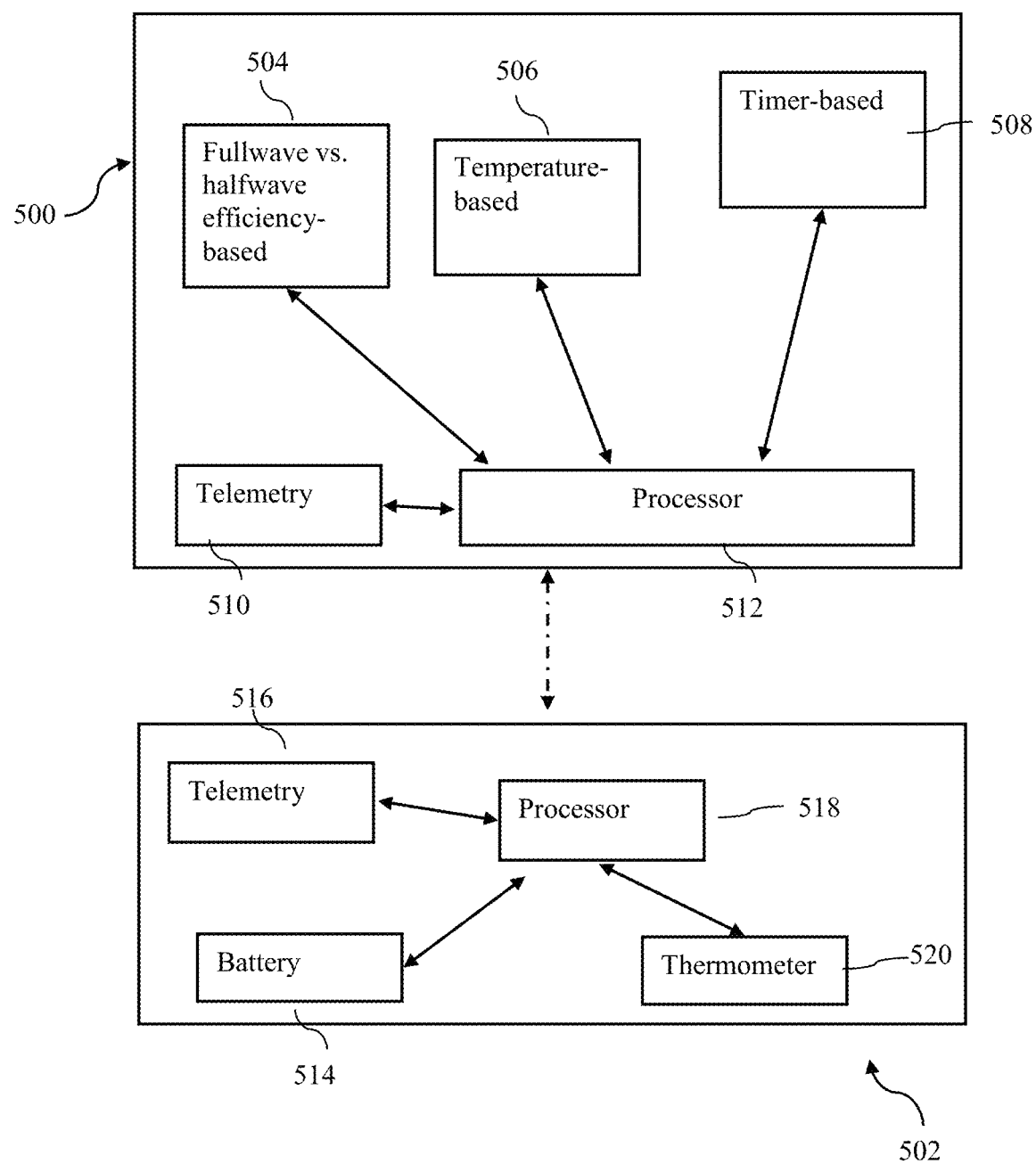
FIG. 10 is a system for wirelessly recharging an implantable device, according to an embodiment.

FIG. 10 depicts a system for wirelessly recharging an implantable device, according to an embodiment. FIG. 10 depicts two components: a wireless recharger 500, and an implanted device 502. The implanted device 502 is recharged by the wireless recharger 500, as indicated by the dashed arrows connecting those components.

An implanted device 502 can include components that determine which mode of operation is appropriate for the rectification of a signal coming from the wireless recharger 500, including a fullwave vs. halfwave efficiency-based module 504, a temperature-based module 506, and a timer-based module 508. Each of these three modules can independently determine whether there is a reason to switch operation mode, as described above. For example, fullwave vs. halfwave efficiency-based module 504 can determine based on received telemetry from the implanted device 502 which rectification mode will more quickly charge the implanted device 502. Similarly, temperature-based module 506 can determine whether the device should operate in fullwave or halfwave rectification mode, or other parameters of recharging such as voltage and frequency of operation of the device, to manage heat within the system and ensure that rapid recharging does not cause uncomfortable or damaging levels of heating. Timer-based module 508 can be used to switch modes of operation after some predetermined amount of time, even if there is no data regarding efficiency or heating that would otherwise cause the switch to be made.

The three modules 504, 506, and 508 can each be operated either independently, or based on data received from the device 502. Data from the device 502 can be acquired via telemetry 510, which facilitates communication between the recharger 500 and the device 502. In embodiments, telemetry 510 can include an antenna configured to emit the recharging field, or in other embodiments two separate antennae can be used, one for communication and the other for the recharging field.

These functions can be coordinated by a processor 512, which routes telemetry signals from telemetry module 510 to the appropriate modules 504, 506, and 508, and which operates the appropriate charging mode by varying the voltage and switches of the antenna for recharging signal as described above with respect to FIG. 6.

Implanted device 502 includes corresponding componentry to carry out the functions described above. In particular, as shown in FIG. 10, device 502 includes a battery 514 that is being recharged, as well as telemetry module 516. These components can each communicate with a processor 518 that can determine, for example, the charge current at the battery 514, and send that information back to the wireless recharger 500 via telemetry 516. An optional thermometer 520 is also shown in FIG. 10, which further communicates with processor 518 and can be used by temperature-based module 506 to detect when changing frequency, voltage, or rectification mode would be beneficial to prevent overheating of the implanted device 502. In other embodiments, thermometer 520 can be omitted and a model of heat generated can be used instead.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

Figure 11A:
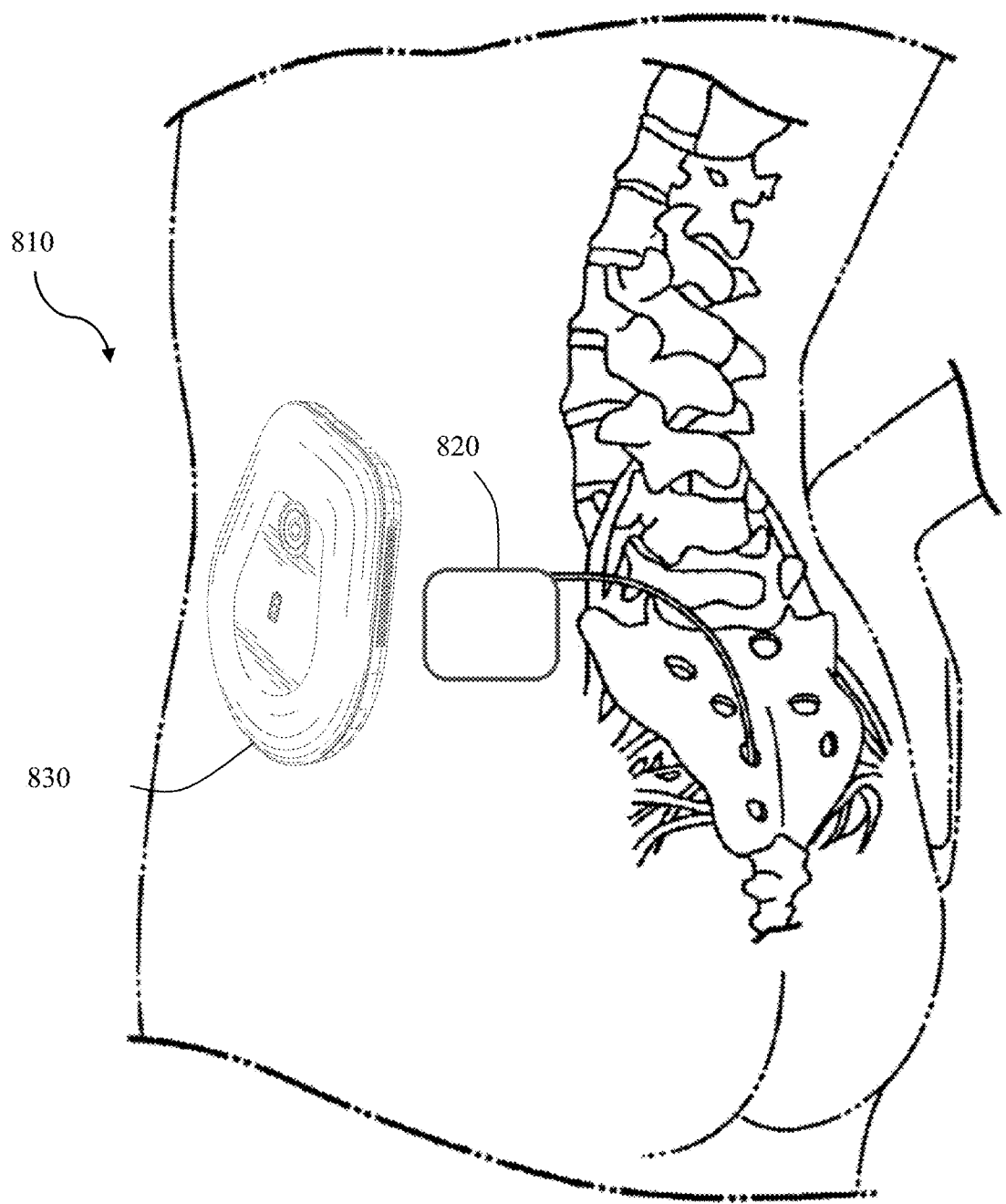
FIG. 11A is a schematic of a sacral nerve stimulation system according to an embodiment.
Figure 11B:
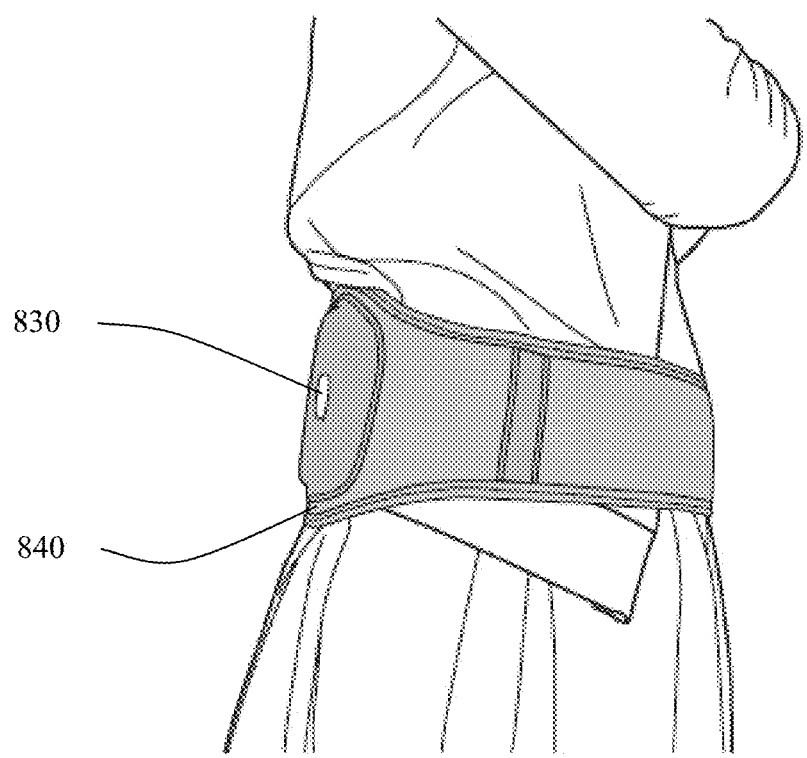
FIG. 11B is a schematic of a sacral nerve stimulation system with a wearable belt according to an embodiment.

In an example, embodiments of the present disclosure may be used as part of a system for treating pelvic health conditions including incontinence, overactive bladder, pelvic pain or other pelvic floor disorders. Referring to FIGS. 11A-B, embodiments of the present disclosure can be implemented as part of a sacral nerve stimulation system 810, including a rechargeable implantable nerve stimulation device 820 and an external recharger 830, wherein external recharger 830 can be positioned on or proximate to skin of the patient over the location of implantable nerve stimulation device 820 to facilitate recharging. Referring to FIG. 11B, external recharger 830 may also be wearable on the patient such as with a belt 840.

Figure 12:
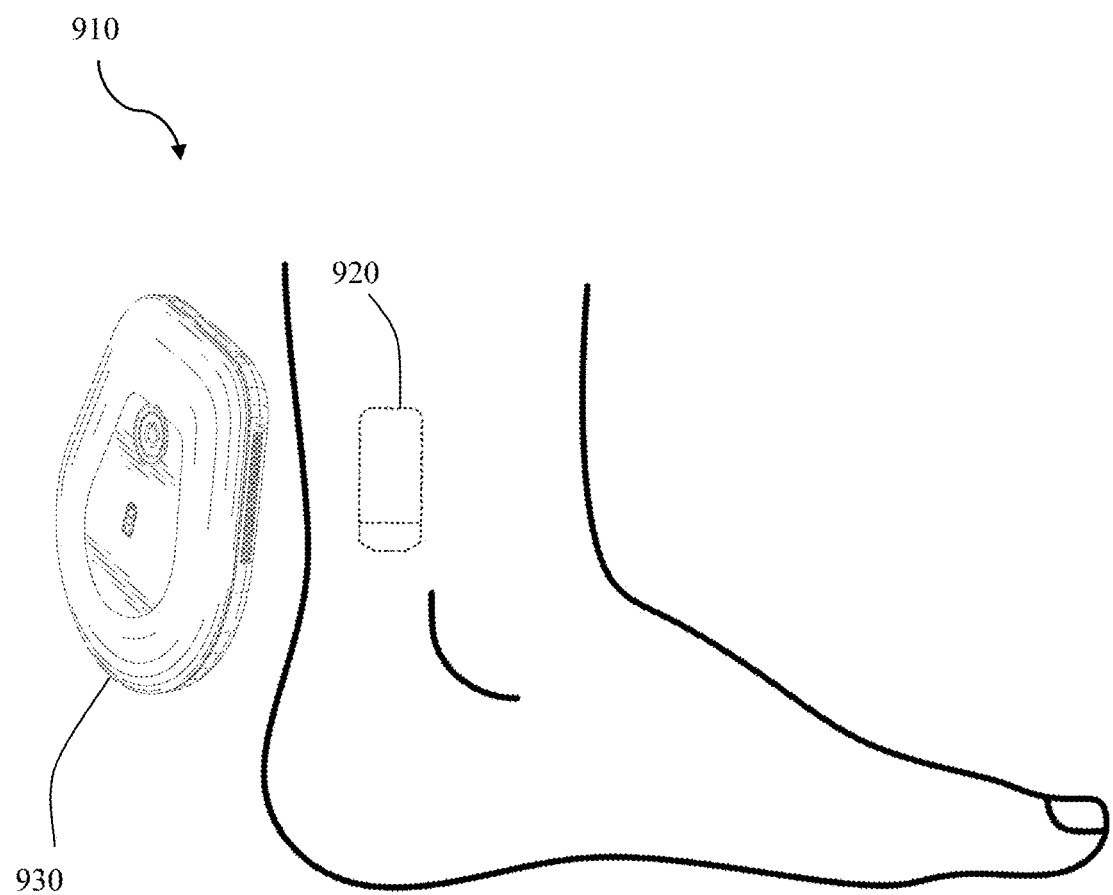
FIG. 12 is a schematic of a tibial nerve stimulation system according to an embodiment.

Referring to FIG. 12, in another example pertaining to treatment of pelvic health disorders, embodiments of the present disclosure may be implemented as part of a tibial nerve stimulation system 910, including an implantable tibial nerve stimulation device 920 and an external recharger 930, wherein external recharger 930 can be positioned on or proximate to skin of the patient over the location of implantable nerve stimulation device 920 to facilitate recharging. Tibial nerve stimulation system 910 may also include a wearable ankle cuff to hold external recharger 930 in position on an ankle of a patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An external charging device comprising:
   a first antenna configured to output a recharge signal;
   a second antenna configured to transmit and receive telemetry signals;
   a telemetry module configured to receive a level of implantable medical device battery charge current from the second antenna; and
   a processor coupled to the telemetry module, the first antenna, and the second antenna, wherein the processor is configured to:
   direct the first antenna to output the recharge signal, and
   direct the second antenna to output instructions to configure the rectification mode of a corresponding implanted device to fullwave or halfwave based upon the level of implantable medical device battery charge current.

2. The wireless recharger of claim 1, wherein the first antenna and the second antenna are a common antenna, and wherein the processor is configured to direct the common antenna to output the recharge signal and the instructions at different times.

3. The wireless recharger of claim 1, wherein the first antenna and the second antenna are a common antenna, and wherein the processor is configured to combine the output instructions and the recharge signal for simultaneous transmission.

4. The external charging device of claim 1, wherein the processor is configured to output the instructions based upon the level of implantable medical device battery charge current and a hysteresis factor.

5. The external charging device of claim 1, wherein the first antenna, the second antenna, the telemetry module, and the processor are arranged in a housing configured for use in a sacral nerve stimulation system.

6. The external charging device of claim 5, wherein the housing is shaped to be wearable in a belt.

7. The external charging device of claim 1, wherein the first antenna, the second antenna, the telemetry module, and the processor are arranged in a housing configured for use in a tibial nerve stimulation system.

8. A method of wirelessly recharging an implantable medical device, the method comprising:
   (a) emitting a recharging signal at an antenna of a wireless recharger;
   (b) collecting telemetry data at the wireless recharger corresponding to a level of charge current in the implantable medical device; and (c) transmitting an output instruction from the wireless recharger to the implanted medical device including an instruction for a rectification mode, wherein:
the output instruction is a fullwave rectification instruction when the charge current is greater than a threshold, and;
the output instruction is a halfwave rectification instruction when the charge current is less than the threshold.

9. The method of claim 8, wherein the threshold is based upon the charge current plus or minus a hysteresis value.

10. A system comprising:
a wireless recharger including an antenna configured to output a recharge signal and a telemetry module configured to receive a level of charge current in a battery;
an implanted device including:
a battery;
a device telemetry module configured to transmit a level of charge current in the battery; and
a processor configured to direct the implanted device to operate in a fullwave rectified wireless signal or a halfwave rectified wireless signal based upon the level of charge current.

11. The system of claim 1, wherein a processor is arranged in the wireless recharger.

12. The system of claim 10, wherein:
the implanted device is configured to receive the recharge signal and operate in any of at least two modes of rectification of the recharge signal to charge the implanted device; and
the processor is configured to determine the optimal rectification mode for the implant to be operating according to an algorithm.

13. The system of claim 12, wherein the processor applies the algorithm to compare a charge current in the implanted device against a threshold plus or minus a hysteresis value to determine which rectification mode is more optimal.

14. The system of claim 12, wherein the processor is configured to compare a peak voltage of the rectified recharge signal plus or minus a hysteresis value to operate the implanted device in the rectification mode that results in greater charge current.

15. The system of claim 12, wherein the processor is configured to compare a sensed magnetic field at the implanted device to a threshold to operate the implanted device in the rectification mode that results in greater charge current.

16. The system of claim 12, wherein the processor is a microcontroller arranged within the implanted device.

17. The system of claim 12, wherein the antenna is configured to receive information pertinent to the optimal rectification mode transmitted by the implanted device at an out-of-band frequency such that the recharge signal can be maintained continuously by the external charging device.

18. The system of claim 17, wherein the antenna is configured to receive information pertinent to the optimal rectification mode that is superimposed with the recharge signal.

19. The system of claim 10, wherein the implanted device includes a charge current detection circuit configured to detect the level of charge current.

20. The system of claim 10, further comprising a belt configured to hold the wireless recharger.

* * * * *